United States Patent [19]

Hourihan et al.

[11] Patent Number: 4,725,431

[45] Date of Patent: Feb. 16, 1988

[54] METHOD FOR THE PREPARATION OF WATER-IN-OIL EMULSION ANTIPERSPIRANTS

[75] Inventors: Joseph C. Hourihan, Little Falls, N.J.; Helga Krevald, Tarrytown, N.Y.

[73] Assignee: American Cyanamid Company, Stamford, Conn.

[21] Appl. No.: 815,284

[22] Filed: Dec. 26, 1985

Related U.S. Application Data

[63] Continuation of Ser. No. 621,872, Jun. 15, 1984, abandoned, which is a continuation of Ser. No. 353,733, Mar. 1, 1982, abandoned.

[51] Int. Cl.$^4$ .......................... A61K 7/32; A61K 7/34; A61K 7/38
[52] U.S. Cl. ............................. 424/66; 424/DIG. 5; 424/68
[58] Field of Search ................ 424/68, 66, 65, DIG. 5

[56] References Cited

U.S. PATENT DOCUMENTS

| | | | |
|---|---|---|---|
| 3,541,205 | 11/1970 | Hardigan | 424/65 |
| 4,229,432 | 10/1980 | Geria | 424/DIG. 5 |
| 4,234,450 | 11/1980 | Hirayama et al. | 424/DIG. 5 |
| 4,252,789 | 2/1981 | Broad | 424/DIG. 5 |
| 4,264,586 | 4/1981 | Callingham et al. | 424/68 |
| 4,265,878 | 5/1981 | Keil | 424/DIG. 5 |
| 4,268,499 | 5/1981 | Keil | 424/68 |
| 4,280,994 | 7/1981 | Turney | 424/DIG. 5 |
| 4,302,443 | 11/1981 | de Navame et al. | 424/DIG. 5 |
| 4,350,605 | 9/1982 | Hughett | 424/68 |

FOREIGN PATENT DOCUMENTS

0081810  6/1980  Japan ............................. 424/DIG. 5

*Primary Examiner*—Dale R. Ore
*Attorney, Agent, or Firm*—C. J. Fickey

[57] ABSTRACT

Method for preparing an antiperspirant composition of the water-in-oil emulsion type having improved application and aesthetic properties which comprises emulsyfing the aqueous phase in the oil phase in the presence of about 1 to 3% by weight of at least one $C_{12}$ to $C_{20}$ saturated fatty acid ester of polyglycerol containing about 2 to 10 repeating glycerol units.

5 Claims, No Drawings

METHOD FOR THE PREPARATION OF WATER-IN-OIL EMULSION ANTIPERSPIRANTS

This application is a continuation of application Ser. No. 621,872, filed June 15, 1984, now abandoned, which is a continuation of Ser. No. 353,733, filed Mar. 1, 1982, now abandoned.

The present invention relates to improvements in water-in-oil emulsions. More particularly, it relates to improvements in the preparation of water-in-oil emulsion type antiperspirant compositions. Still more particularly, it relates to improvements in antiperspirant compositions, especially antiperspirant sticks, which result when an aqueous solution of an antiperspirant astringent is emulsified in a waxy hydrophobic matrix which may contain a volatile silicone liquid.

Water-in-oil emulsion type antiperspirant sticks are known, but they have not met with much success. This is due, primarily, to the fact that they have poor application properties, that is, they exhibit a draggy feel when applied. Moreover, they are not very efficacious and they lack aesthetic appeal. Nevertheless, there has been a trend toward antiperspirant compositions which exhibit a "dry" feel and a number of compositions have been reported, both suspension types and water-in-oil emulsion types, which comprise a volatile silicone liquid to provide the dry feel.

Gee et al, U.S. Pat. No. 4,122,029, and Keil, U.S. Pat. No. 4,265,878, describe water-in-oil emulsion type antiperspirant sticks in which an aqueous solution of an astringent, such as aluminum chlorohydrate, is emulsified in a hydrophobic continuous phase, for example, a volatile silicone. Gee et al use a silicon-free water-in-oil surfactant having an HLB value of 2 to 10 and certain polydiorganosiloxane-polyoxyalkylene block copolymers as emulsifying agents. Keil discloses that the primary surfactant, that is, the polydiorganosiloxane-polyoxyalkylene block copolymers, and the volatile silicone liquid, are more compatible with a wax base comprising a solid alkanoic acid (for example, stearic acid), a waxy ester (for example, spermaceti wax) and, optionally, a solid alkanol in limited amounts, than they are with the conventionally used solid alkanols.

Cosmetic sticks of the water-in-oil emulsion type are also disclosed by Fujiyama et al, British Pat. No. 1,442,426. These sticks, which are primarily lipsticks, are reported to have improved moistening, spreadability, and lustering properties. Essentially, Fujiyama's compositions comprise water, a polyhydroxy compound (for example, mannitol, glycerol), a non-ionic surfactant selected from oleic acid esters and oleyl ethers of polyhydric alcohols, and a cosmetic base (for example, a wax).

The preparation of water-in-oil emulsions, as in Fujiyama et al, has typically involved the use of a non-ionic oleic acid ester or oleyl ether of a polyhydric alcohol as the emulsifying agent. These include such commonly used surfactants as glycerol monooleate, sorbitol monooleate, glycerol dioleate, and the like. These unsaturated esters and ethers, when used to prepare water-in-oil emulsion type antiperspirant sticks tend to impart an odor and result in rancidity.

Thus, there is a need for a method for the preparation of water-in-oil emulsion type antiperspirant compositions which exhibit improved application properties and aesthetic appeal.

In accordance with the present invention, it has been found that if a water-in-oil emulsion type antiperspirant composition is prepared using a low concentration of at least one $C_{12}$–$C_{20}$ saturated fatty acid ester of polyglycerol, the resulting emulsion will be near the breaking point and will break at the time of application, or slightly thereafter, to provide enhanced application properties. Moreover, the emulsifiers do not impart an odor and have no tendency to become rancid.

It is believed that it is necessary for the emulsion to break at the time of application of the antiperspirant, or slightly thereafter, in order for the active astringent to be effective in reducing perspiration. The $C_{12}$ to $C_{20}$ saturated fatty acid esters of polyglycerol, when used at low levels of concentration, that is, from about 1 to 3% by weight, based on the weight of the composition, provide an emulsion near the breaking point and provide efficient delivery of the astringent to the axilla. The antiperspirant efficacy of the resulting product is improved relative to comparable compositions prepared using the conventional oleate type emulsifiers. Thus, although efficacious water-in-oil emulsion antiperspirants may be prepared using the conventional oleate type emulsifiers, the use of the $C_{12}$ to $C_{20}$ saturated fatty acid esters of polyglycerol permit the attainment of an equal level of efficacy by the use of lower levels of astringent.

The emulsifiers useful in the present invention are $C_{12}$ to $C_{20}$ saturated fatty acid esters of polyglycerol oligomers, wherein the number of repeating glycerol units in the oligomeric chain range from about 2 to about 10. These include the laurate, myristate, palmitate, stearate, isostearate, and eicosinoate esters. Preferably, the emulsifier will be a higher ester, that is, a palmitate, stearate or isostearate, of polyglycerol oligomers containing from about 3 to 6 repeating glycerol units. Preferred emulsifiers include polyglyceryl-4-stearate (also known as tetraglycerylstearate), polyglyceryl-4-isostearate and polyglyceryl-4-palmitate.

The amount of emulsifier used should be in the range of about 1 to 3% by weight, based on the weight of the composition. It is important that the concentration used will be such as to achieve an emulsion which is near the breaking point. Of course, the concentration will be dependent on the type of oils and waxes used in the hydrophobic phase. If too little is used, the emulsion will not form or will be unstable; if too much is used, the emulsion will not break readily and will not release the astringent efficiently.

Although the present invention will be described with respect to the preparation of a water-in-oil emulsion type antiperspirant stick, it will be recognized that water-in-oil emulsion type antiperspirants may take other forms, such as creams and lotions, and that the method of the invention is applicable to the preparation of water-in-oil emulsions in general and to their use in other products, such as lipsticks, pharmaceutical preparations, and the like.

Essentially, in the preparation of water-in-oil emulsion type antiperspirant sticks, an aqueous solution of an antiperspirant astringent compound is emulsified, by conventional emulsification techniques, in a hydrophobic medium by the use of a suitable emulsifying agent.

The term "hydrophobic medium," as used herein, means any of the water-insoluble oils, waxes, fatty alcohols, fatty acid esters, fatty acid amides, metal salts of alkanoic acids, volatile silicones, and the like, commonly used in the cosmetic art to prepare cosmetic emulsions, so long as they are compatible with each other and with the emulsifying agent. In the present invention, a preferred hydrophobic medium is a waxy matrix comprising a volatile cyclic polydimethyl siloxane oligomeric liquid, often referred to in the art as a volatile silicone.

The cyclic tetramer (I, 2,4,6,8-octamethylcyclotetrasiloxane), cyclic pentamer (II, 2,4,6,8,10-decamethylcyclopentasiloxane) and cyclic hexamer (III, 2,4,6,8,10,12-dodecamethylcyclohexasiloxane), and mixtures thereof, are commonly available commercially (Dow Corning).

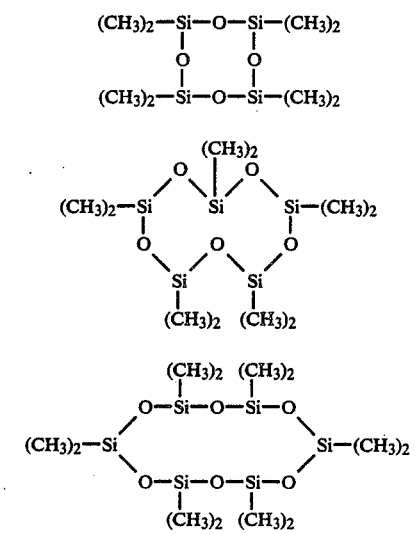

The waxy matrix may comprise any of the waxes or wax-like compounds commonly used in sticks, but preferably the waxy matrix of the present invention will comprise a solid fatty alcohol, such as stearyl alcohol or cetyl alcohol, or mixtures thereof, and, optionally, a solid alkanoic acid, for example, stearic acid.

Other commonly used ingredients may be incorporated into the composition to achieve certain desirable effects, such as mineral oil, other emollients, fragrances, dyes, and the like.

Among the useful astringents are aluminum sulfate, aluminum chloride, aluminum chlorohydrate, aluminum sulfocarbolate, aluminum-zirconium chlorohydrate, zinc chloride, zinc sulfocarbolate, zinc sulfate, zirconium salts, such as zirconium chlorohydrate, combinations of aluminum chloride and aluminum chlorohydrate or aluminum-zirconium chlorohydrate, aluminum-zirconium chlorohydroglycine, and the like. Aluminum chlorohydrate is preferred and is preferably used as a 50% aqueous solution.

The active ingredient may be used in amounts up to about 30% by weight, on a solids basis although amounts normally used range from about 15 to 25% by weight, on a solids basis. In any case, sufficient should be used to achieve at least a 20% reduction in perspiration in 50% of the population.

The following water-in-oil emulsion antiperspirant stick composition has good application properties and high antiperspirant efficacy.

EXAMPLE 1

|  | Percent by Weight |
| --- | --- |
| Aluminum chlorohydrate, 50% aq. soln. | 50.0 |
| Polyglyceryl-4-isostearate | 2.0 |
| 2-Methyl-2,4-pentanediol | 2.0 |
| Stearic acid | 2.0 |
| Stearyl alcohol | 17.0 |
| Cyclic silicone pentamer | 26.0 |
| Mineral oil | 1.0 |
|  | 100.0 |

Similar results are obtained when polyglyceryl-4-isostearate is replaced by polyglyceryl-2-isostearate, polyglyceryl-3-isostearate, polyglyceryl-3-stearate, polyglyceryl-4-palmitate, polyglyceryl-5-laurate, and polyglyceryl-3-myristate.

EXAMPLE 2

| Al Zirconium chlorhydrex | 25.0 |
| --- | --- |
| Deionized Water | 25.0 |
| Cyclic silicone pentamer | 22.0 |
| Stearyl Alcohol | 20.0 |
| Hexylene Glycol | 3.0 |
| Polyglyceryl 4 isostearate | 1.5 |
| Polyglyceryl 3 diisostearate | 1.5 |
| Stearic Acid | 2.0 |
|  | 100.0 |

EXAMPLE 3

| Al Chlorohydrate 50% aq. | 50.0 |
| --- | --- |
| Cyclic silicone pentamer | 21.5 |
| Stearyl Alcohol | 20.0 |
| Hexylene glycol | 3.0 |
| Polyglyceryl 4 isostearate | 2.0 |
| Polyglyceryl 2 isostearate | 1.0 |
| Isostearic Acid | 2.0 |
| PPG Myristyl Ester | 0.5 |
|  | 100.0 |

EXAMPLE 4

| Al Chlorohydrate 50% aq. | 55.0 |
| --- | --- |
| Cyclic Silicone pentamer | 19.0 |
| Stearyl Alcohol | 19.0 |
| Hexylene glycol | 2.0 |
| Stearic Acid | 2.0 |
| Polyglyceryl 3 isostearate | 3.0 |
|  | 100.0 |

What is claimed is:

1. In a method for the preparation of an antiperspirant stick composition of the water-in-oil emulsion type antiperspirant composition having improved application properties, wherein an aqueous solution of an antiperspirant astringent compound is emulsified in a hydrophobic medium selected from the group consisting of water-insoluble oils, waxes, fatty alcohols, fatty acid esters, fatty acid amides, metal salts of alkanoic acid and volatile, silicones as a continuous phase, wherein the improvement comprises emulsifying said aqueous phase in said hydrophobic phase in the presence of from about 1 to 3 percent by weight, based on the weight of said antiperspirant composition, of at least one $C_{12}$–$C_{20}$ saturated fatty acid ester of polyglycerol, said polyglycerol containing from about 2 to 10 repeating glycerol units.

2. A method according to claim 1 wherein said hydrophobic phase comprises a volatile cyclic polydimethyl siloxane liquid.

3. A method according to claim 2 wherein said hydrophobic phase is a waxy matrix comprising a volatile cyclic polydimethyl siloxane liquid.

4. A method according to claim 3 wherein said hydrophobic phase additionally comprises a solid fatty alkanol.

5. Methods according to claim 1 to 4 wherein said emulsifying agent is a stearate or isostearate ester of polyglycerol.

* * * * *